United States Patent [19]

Landy et al.

[11] Patent Number: 4,600,013
[45] Date of Patent: Jul. 15, 1986

[54] INTRACRANIAL PRESSURE MONITORING PROBE

[76] Inventors: Howard Landy, 10940 SW. 125 St., Miami, Fla. 33176; Lawrence Landy, 6866 Sunrise Ter., Coral Gables, Fla. 33133

[21] Appl. No.: 608,204

[22] Filed: May 8, 1984

[51] Int. Cl.$^4$ .............................................. A61B 5/00
[52] U.S. Cl. .................................................. 128/748
[58] Field of Search .................. 128/748, 903, 303 R, 128/303.1

[56] References Cited

U.S. PATENT DOCUMENTS

| 4,062,354 | 12/1977 | Taylor et al. | 128/748 X |
| 4,246,908 | 1/1981 | Inagahi et al. | 128/748 |

FOREIGN PATENT DOCUMENTS

| 2720455 | 11/1978 | Fed. Rep. of Germany | 128/748 |
| 985553 | 7/1951 | France . | |
| WO83/03190 | 9/1983 | PCT Int'l Appl. | 128/748 |
| 1598378 | 9/1981 | United Kingdom . | |

OTHER PUBLICATIONS

"PMS Philadelphia Medical Specialties, Inc."
"Intracranial Subarachnoid Pressure Monitoring in Children", James et al., vol. 3, *Surg. Nevrol., Jun. 1975, pp. 313-315.*
"Methodology for Intraventricular and Subarachnoid Continuous Recording of Intracranial Pressure in Clinical Practice", *ACTA Neurothirurgiea*, vol. 33, pp. 45-51 (1976).
"Radionics ® Neurosurgical Instruments" Advertisement.
"Assessment of Leeds Device for Monitoring Intracranial Pressure", Dearden et al., *J. Neurosurg.*, vol. 60, pp. 123-129, Jan. 1984.
"A Clinical Comparison of Subdural Screw Pressure Measurements with Ventricular Pressure", Mendelow et al., vol. 58, *J. Neurosurg.* pp. 45-50, Jan., 1983.
Codman Catalog No. 80-1182, p. 271.
"A Subarachnoid Screw for Monitoring Intracranial Pressure", Vries et al., *J. Neurosurg.*, vol. 39, Sep. 1973, pp. 416-419.
"Modification of the Richmond Subarachnoid Screw for Monitoring Intracranial Pressure"; *J. Neurosurg.*, vol. 60, pp. 1102-1103, May, 1984.

*Primary Examiner*—Edward M. Coven
*Attorney, Agent, or Firm*—Lowe, Price, LeBlanc, Becker & Shur

[57] ABSTRACT

A probe for enabling intracranial pressure in the subarachnoid space to be determined is inserted through an opening in the scalp, into and through the outer table, diploe and inner table of the skull and dura mater and arachnoid into the subarachnoid space. The probe comprises a threaded shaft having a lumen communicating with openings at the end of the shaft into the subarachnoid space so that the fluid is coupled into and through the shaft openings into the shaft bore and the pressure of the fluid can be coupled then to a pressure transducer. The threaded portion of the shaft has a length sufficient to threadingly engage the outer table, the diploe and the inner table. A lock nut threadingly engages the threaded portion and is dimensioned to fit into the scalp opening to bear against the hard outer table. The shaft threads engaging the outer and inner tables and the diploe cooperate with the lock nut to securely hold the shaft in place.

17 Claims, 4 Drawing Figures

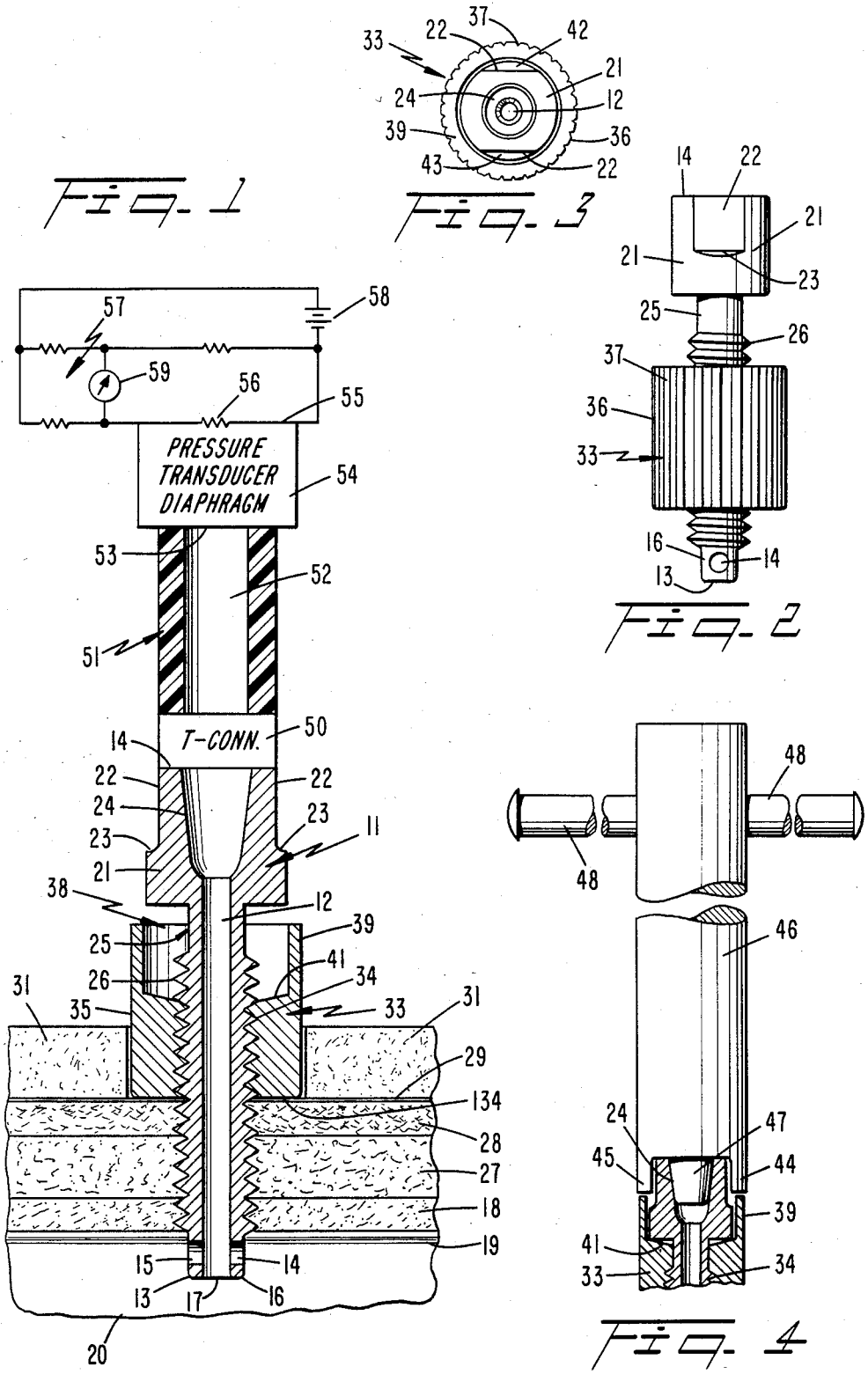

INTRACRANIAL PRESSURE MONITORING PROBE

TECHNICAL FIELD

The present invention relates generally to probes for enabling intracranial pressure in the subarachnoid space to be determined and, more particularly, to a probe including a lock nut for threadingly engaging a threaded portion of a threaded shaft and wherein the nut is dimensioned to fit into an opening of the scalp to bear against the hard outer table of the skull to securely hold the shaft, which contains a fluid pressure communicating passage, in place.

BACKGROUND ART

It has been the practice to monitor intracranial pressure of patients suffering from severe brain injuries for many years. Several different structures have been proposed and adopted for this purpose. The structures generally include a shaft, in the form of a bolt or screw, having a central passage for coupling fluid pressure from the subarachnoid space to a pressure transducer which can be selectively connected to a tube adapted to be connected to the shaft. The shaft extends through an opening in the scalp, through the three layers of the skull, i.e., the outer table, the diploe, and the inner table, and through the dura mater and the arachnoid to the subarachnoid space.

One prior art subarachnoid screw for monitoring intracranial pressure includes a standard luer lock and a hexagonal collar for insertion at the proximal end of the screw. Threads on the distal end of the screw fit a quarter inch twist drill hole. A glass wool wick may be placed in a lumen of each screw before insertion of the screw to prevent occlusion at the tip of the screw. The screw is inserted by making a twist drill hole in the skull of the patient through a scalp incision under local anesthesia. The thereby exposed dura mater is nicked with a knife under direct vision by the surgeon and removed with a small angled currette, to open the dura and the arachnoid. The screw is threaded into the twist drill hole with a hexagonal screwdriver to a location that places the tip of the screw slightly below (preferably 1 mm.) the dura surface. The incision in the scalp is closed around the shaft screw with sutures and a small sterile dressing is placed around the shaft. The screwdriver is formed as a shaft having a pair of diametrically opposed tines which engage the hexagonal collar on the screw shaft. The screwdriver includes a pair of diametrically opposed rods which form a handle enabling the screwdriver to be turned by hand.

The aforementioned prior art structure, however, does not remain securely attached to the skull during the usual period of time for which it is used for intracranial pressure monitoring, a period most commonly from three to seven days. The thread has insufficient length to be securely screwed into most skulls. The screw must be attached to a stopcock, which when manipulated causes movement and loosening of the screw. The combination of the screw and stopcock produces a device which extends for a considerable distance above the scalp and is therefore easily jarred loose.

A further intracranial subarachnoid pressure monitoring device includes a bolt having a threaded section screwed into the skull of the patient. At the end of the threaded portion is a smooth portion having a diameter less than the threaded portion and containing an orifice for coupling fluid from the subarachnoid space into a passage extending longitudinally through the bolt. At the other end of the threaded portion is a radially extending flange that serves as a seal for a twist drill hole that is made by the surgeon into the skull. Longitudinally spaced along the bolt from the flange is a local widening for receiving a wrench which is used to drive the bolt into the skull. Extending from the local widening is a stub shaft which forms a female adapter for intravenous tubing. The intravenous tubing is connected to a pressure transducer, whereby the fluid pressure coupled through the bolt channel is coupled to the pressure transducer.

The bolt is inserted by making an incision through the scalp to the skull and then boring a hole through the skull, without penetrating the dura mater. The bolt is placed into a bolt handle and then screwed into the bored hole until the bolt flange closes snugly against the skull outer table to enhance stability. The dura mater is then perforated several times with a wire probe to insure communication of the passage in the bolt with the subarachnoid space. The incision in the scalp is then closed with sutures. Thereafter, the intravenous tubing is connected to the bolt.

This prior art structure has a lower profile than the previously described prior art device. However, the flange is not adjustable to accommodate skulls having differing thicknesses and the bolt requires a large scalp incision for insertion.

Both of these generally used prior art screws or bolts frequently become occluded by a blood clot or dura mater fragments.

A further prior art intracranial probe for monitoring subarachnoid pressure has a self-tapping thread capped intracranial end capped by an end plate with side ports providing fluid communication between the intracranial space and a tube leading to a monitoring device. Prior to inserting this prior art probe into the subject, a formal burr hole is made in the skull. The hole has a relatively large diameter, about ¾ inch, and requires significantly more operative effort than a small twist drill hole.

It is, accordingly, an object of the present invention to provide a new and improved subarachnoid probe for monitoring intracranial pressure.

A further object of the invention is to provide a new and improved probe for enabling intracranial pressure in the subarachnoid space to be determined more accurately over the required time period.

Still a further object of the invention is to provide a probe for enabling intracranial pressure in the subarachnoid space to be determined, wherein the probe is stably mounted in the skull for the required period of time.

Still a further object of the invention is to provide a new and improved probe for enabling intracranial pressure in the subarachnoid space to be determined, wherein the probe is capable of accommodating skulls having different thicknesses.

Still a further object of the invention to provide a new and improved probe for enabling intracranial pressure in the subarachnoid space to be determined, wherein the probe includes openings into a passage so that the likelihood of occlusions is considerably reduced.

BRIEF DESCRIPTION

In accordance with the present invention, a probe for enabling intracranial pressure in the subarachnoid space to be determined includes a lock nut for threadingly engaging a threaded portion of a shaft having a longitudinal bore, i.e. lumen, communicating with opening means at the intracranial end of the shaft. The opening means at the intracranial end of the shaft communicates into the subarachnoid space so that the subarachnoid fluid is coupled into and through the shaft opening means into the lumen so that the pressure can be coupled to a pressure transducer. The threaded shaft portion has a length sufficient to threadingly engage the outer table, the diploe and the inner table of the skull of the patient. The lock nut is dimensioned to fit into the scalp opening to bear against the hard outer table. The shaft threads engaging the outer and inner tables and the diploe cooperates with the nut when the nut is screwed on the threads of the shaft against the outer table to securely hold the shaft in place.

The lock nut which screws down against the outer table of the skull stably holds the probe in place. The long length of the thread allows insertion of the probe into skulls of varying thicknesses. The probe of the present invention, wherein the threaded portion has larger teeth, i.e., larger threads, provides a more secure bite into the skull than the thread employed in the first-mentioned bolt. The bolt of the present invention is as short as possible, while still accommodating a long thread and a lock nut. To maintain a low profile, the outer end of the probe is connected to the male end of a standard T-connector, rather than to a stopcock. The intracranial end of the bolt has two side ports and a bottom port connected to the lumen running the length of the shaft to decrease the frequency of occulsion. The two side ports are diametrically opposed openings in the shaft wall, between the inner end of the shaft and the end of the threaded portion of the shaft.

To insert the probe in situ, the outer end of the shaft includes a boss with a diameter slightly less than the inner diameter of the outer end of the lock nut. The boss and lock nut have cooperating adjacent surfaces. The boss has straight longitudinally extending indented segments that are displaced radially from the bore or lumen for receiving corresponding tines of a driving tool or screwdriver. The boss includes a central opening aligned with the bore for receiving a corresponding stub of the driving tool and through which the subarachnoid fluid pressure is coupled. The lock nut is preferably knurled to be turned by hand.

The above and still further objects, features and advantages of the present invention will become apparent upon consideration of the following detailed description of one specific embodiment thereof, especially when taken in conjunction with the accompanying drawings.

BRIEF DESCRIPTION OF THE DRAWINGS

FIG. 1 is a side sectional view of a subarachnoid probe or screw in accordance with the present invention, as inserted into the scalp and skull of a patient, and in combination with a plastic intravenous tube coupled to a pressure transducer and monitoring device;

FIG. 2 is a side view of the subarachnoid screw illustrated in FIG. 1;

FIG. 3 is a top view of the subarachnoid screw of the invention; and

FIG. 4 is a side sectional view of a subarachnoid screw and a screwdriver therefor, in accordance with the present invention.

BEST MODE FOR CARRYING OUT THE INVENTION

Reference is now made to FIGS. 1-3 of the drawing wherein the subarachnoid intracranial pressure monitoring probe of the present invention is illustrated as including a stainless steel threaded shaft 11, having a central, longitudinally extending, bore or lumen 12 which extends between the proximal and distal ends 13 and 14 of the screw. Lumen 12 is open at the proximal and distal ends of threaded shaft 11. At proximal end 13 shaft 11 has a smooth wall portion 16 in which ports 14 and 15 are diametrically located for communication of subarachnoid fluid to lumen 12. Fluid in the subarachnoid space is also coupled to lumen 12 via opening 17 at the proximal end of threaded shaft 11. The smooth wall portion 16 of threaded shaft 11 extends through the bottom hard inner table 18 of the skull and through dura mater and arachnoid 19 into the subarachnoid region of the head which subsists between the contour of brain 20 and dura mater 19.

The distal end 14 of threaded shaft 11 includes generally cylindrical boss 21 having straight longitudinally extending indented segments 22 to form shoulders 23. Lumen 12 includes an outwardly flared portion 24, as the lumen extends through boss 21. Immediately below boss 21 threaded shaft 11 includes smooth wall segment 25, having approximately the same diameter as smooth wall segment 16.

Between smooth wall segments 16 and 25 is threaded portion 26, having a length sufficient to enable the threaded portion to threadingly engage inner table 18, as well as all of diploe 27 and all of outer table 28 of the skull. In addition, threaded portion 26 extends considerably above outer table 28 and periosteum layer 29, and beyond scalp layer 31. The length of threaded portion 26 is sufficient to enable the threaded portion to extend through all three layers of the skull, as well as through the scalp of patients having differing skull and scalp thicknesses; the length of threaded shaft 11, however, is not so great as to cause the probe to have a "high profile", i.e., the probe does not extend beyond the scalp by an excessive amount. It has been found that a satisfactory length for threaded screw 11 is 1½ inches, and for threaded portion 26 is ¾ inch. Smooth wall portions 16 and 25 are preferably approximately 5/32 inch in length.

Threadingly engaging threaded portion 26 of shaft 11 is stainless steel lock nut 33. Lock nut 33 has a central bore 34 threadingly engaging threaded portion 26 of shaft 11. Lock nut 33 has a planar face 134 for engaging the outer edge of hard outer table 28 of the skull to securely hold shaft 11 in situ. Outer wall 35 of lock nut 33 is knurled with longitudinally extending ridges 36 and grooves 37. At the end of lock nut 33 remote from face 134 is cavity 38, formed by tapered interior face 41 and ring segment 39 that extends longitudinally of the lock nut axis. The inner diameter of ring 39 is slightly greater than the diameter of boss 21 so that the boss can fit into cavity 38.

During initial installation of the probe, shaft 11 is threaded into lock nut 33 so that the walls of boss 21 are within cavity 38. Straight segments 22 fit inside longitudinally extending tines 44 and 45 of stainless steel wrench or screwdriver 46, FIG. 4. Screwdriver 46 also includes a longitudinal central stub 47 which extends into the cavity formed by flared wall 24 in boss 21. Wrench 46 includes radially extending handles 48 at the end of the wrench opposite from tines 44 and 45 and stub 47.

To monitor the fluid pressure in lumen 12, a low compliance, relatively heavy plastic tube 51, is connected to conventional T-connector 50 and is thus fitted onto boss 21. Tube 51 includes an internal passage 52 for coupling fluid from the subarachnoid space immediately above brain 20 of the patient to face 53 of pressure monitoring diaphragm or transducer 54. Mounted on the opposite face 55 of pressure monitoring diaphragm 54 is strain gauge resistor 56. Resistor 56 is connected in Wheatstone bridge circuit 57 that is activated by battery 58 and includes a current responsive indicator 59.

The subarachnoid intracranial pressure monitoring probe of the present invention is inserted into the patient after the frontal scalp is shaved and prepared in a sterile fashion, and an incision approximately 17 millimeters long has been made through the scalp down to the skull at a point 8-10 centimeters posterior to the nasion and 3 centimeters lateral to the midline. The right or left side of the head of the patient is chosen with regard to the type and location of the intracranial pathology and cerebral dominance. The periosteum 29 of the subject is retracted with the end of a knife handle. A 3/16 inch twist drill hole is made, thereby penetrating the full thickness of the calvarium, i.e., all three layers of the skull. The distance from the dura mater 19 to the outer surface of the scalp is measured, preferably using the blunt end of a small drill bit as a gauge. The distance that threaded shaft 11 is to protrude above scalp 31 is equal to 34 mm. minus the distance from dura mater 19 to the outer layer of scalp 31. The dura mater is then carefully perforated with a small drill bit. Threaded shaft 11 is then screwed into the twist drill hole using wrench 46, after tines 44 and 45 and stub 47 of the wrench have been fitted on segments 22 and into the cavity formed by wall 24 when the lock nut abuts against boss 21. Threaded shaft 11 is advanced into the head of the patient by the surgeon turning wrench 46 until the previously ascertained length of bolt is left protruding above the top edge of scalp 31. Screw 11 is then filled with a normal saline solution and connected to plastic tube 51 by T-connector 50. The fluid pressure coupled from the subarachnoid space into lumen 12 is coupled by saline solution in the lumen, T-connector 50 and tube 51 to pressure responsive diaphragm 54.

If an adequate response from indicator 59 is not obtained, the position of screw 11 may be adjusted, or the screw may be irrigated with 0.2-0.5 cm. of a normal saline solution to clear any blood clot occluding lumen 12 or any of openings 14, 15 or 17. Such occlusions are to a large extent obviated or are usually cleared because of the diametric relation of openings 14 and 15, in combination with opening 17. After an adequate response is derived from indicator 59, nut 33 is tightened so that face 134 thereof bears against the outer surface of outer table 28. In this position, scalp 31 surrounds the lower portion of nut 33. A single suture in the end of the incision usually suffices to stop any scalp bleeding. If bleeding from the edge of scalp 31 does not stop as a result of tamponade action of the lock nut, a purse-string stitch is placed around the lock nut. A sterile dressing is then applied around the base of lock nut 33.

While there has been described and illustrated one specific embodiment of the invention, it will be clear that variations in the details of the embodiment specifically illustrated and described may be made without departing from the true spirit and scope of the invention as defined in the appended claims.

I claim:

1. A probe for enabling intracranial pressure in the subarachnoid space to be determined, the probe being inserted through an opening in the scalp, into and through the outer table, diploe and inner table of the skull and dura mater and into the subarachnoid space, the probe comprising:

a threaded shaft having a lumen, opening means at the proximal end of the lumen, the opening means communicating with the lumen and the subarachnoid space so that the subarachnoid fluid is coupled into and through the shaft opening means into the shaft lumen and can be coupled thence to a pressure transducer, the threaded portion of the shaft having a length sufficient to threadingly engage the outer table, the diploe and the inner table, and a lock nut means for threadingly engaging the threaded portion and for bearing against the hard outer table, said lock nut means being dimensioned to fit into the scalp opening the shaft threads engaging the outer and inner tables and the diploe cooperating with threads of the lock nut means when the lock nut means is screwed on the threads of the shaft against the outer table to securely hold the shaft in place.

2. The probe of claim 1 wherein the opening means includes diametrically opposed openings in the shaft wall between the proximal end of the shaft and the end of the threaded portion of the shaft.

3. The probe of claim 2 wherein the lumen has a longitudinal axis extending generally at right angles to the scalp the surface portion containing the opening in the scalp, opening means including an opening in the proximal end of the shaft in line with the lumen longitudinal axis.

4. The probe of claim 3 wherein the proximal end of the shaft containing the opening means and extending through the edge of the inner table adjacent the dura mater has a smooth wall and a smaller diameter than the diameter of the threaded portion.

5. The probe of claim 1 wherein the lumen has a longitudinal axis extending generally at right angles to the scalp the surface portion containing the opening in the scalp, opening means including an opening in the proximal end of the shaft in line with the lumen longitudinal axis.

6. The probe of claim 5 wherein the proximal end of the shaft containing the opening means and extending through the edge of the inner table adjacent the dura mater has a smooth wall and a smaller diameter than the diameter of the threaded portion.

7. The probe of claim 1 wherein the proximal end of the shaft containing the opening means and extending through the edge of the inner table adjacent the dura mater has a smooth wall and a smaller diameter than the diameter of the threaded portion, the opening means including an opening at the proximal end of the shaft in line with the lumen longitudinal axis and plural openings at right angles to the lumen longitudinal axis in the smooth wall having the smaller diameter.

8. The probe of claim 1 wherein the lock nut means includes a cavity at an end opposite from an end bearing against the hard outer table, the distal end of the shaft including a boss with a diameter slightly less than the diameter of the cavity so that the boss can be driven into the cavity, the boss having surfaces for receiving corresponding tines of a driving tool.

9. The probe of claim 8 wherein the boss includes a central opening aligned with the lumen for receiving and interlocking a corresponding stub of the driving tool and for enabling the fluid pressure to be coupled to the transducer.

10. The probe of claim 9 wherein the lock nut means is knurled to be turned by hand.

11. The probe of claim 1 wherein the lock nut means has a length such that it extends beyond the scalp when the lock nut bears against the hard outer table so the lock nut means can be turned by hand.

12. The probe of claim 11 wherein the lock nut means is knurled to facilitate the turning by hand.

13. In combination, a probe for enabling intracranial pressure in the subarachnoid space to be determined, the probe being inserted through an opening in the scalp, into and through the outer table, diploe and inner table of the skull and dura mater and into the subarachnoid space, the probe comprising:

a threaded shaft having a lumen communicating with opening means at the proximal end of the lumen into the subarachnoid space so that the subarachnoid fluid is coupled into and through the shaft opening means into the lumen and can be coupled thence to a pressure transducer, the threaded portion of the shaft having a length sufficient to threadingly engage the outer table, the diploe and the inner table, and lock nut means for threadingly engaging the threaded portion and for bearing against the hard outer table, said lock nut means being dimensioned to fit into the scalp opening the shaft threads engaging the outer and inner tables and the diploe cooperating with the lock nut means when the lock nut means is screwed on the threads of the shaft against the outer table to securely hold the shaft in place, the lock nut means including a cavity in a surface opposite from a surface thereof which bears against the outer table;

14. The combination of claim 13 wherein the tines on the driving tool are diametrically opposed for engaging diametrically opposed outer surfaces of the boss.

15. A probe for enabling intracranial pressure in the subarachnoid space to be determined, the probe being inserted through an opening in the scalp, into and through the outer table, diploe and inner table of the skull and dura mater and into the subarachnoid space, the probe comprising:

a threaded shaft having a longitudinal axis generally at right angles to the scalp surface portion containing the opening, the shaft including a longitudinally extending lumen extending in the same direction as the longitudinal axis, the threaded shaft having opening means at the proximal end of the lumen, the opening means communicating with the lumen and the subarachnoid space so that the subarachnoid fluid is coupled into and through the shaft opening means into the shaft lumen and can be coupled thence to a pressure transducer, the threaded portion of the shaft having a length sufficient to threadingly engage the outer table, the diploe and the inner table, and lock nut means for threadingly engaging the threaded portion and for bearing against the hard outer table, said lock nut means being dimensioned to fit into the scalp opening, the lock nut means including a planar face at right angles to the longitudinal axis bearing against the hard outer table and a cylindrical side wall that fits into the opening, frictional forces being provided by: (a) the lock nut means planar face engaging the outer table, (b) the lock nut means threads cooperating with the shaft threads, and (c) the shaft threads engaging the outer and inner tables and the diploe; said frictional forces being the only forces holding the shaft in place in the opening, the threads remaining intact and not subjected to damage when the lock nut means is screwed onto the threaded shaft and screwed off of the threaded shaft.

16. The probe of claim 15 wherein the lock nut means includes a cavity at an end opposite from the planar face bearing against the hard outer table, the distal end of the shaft including a boss with a diameter slightly less than the diameter of the cavity so that the boss can be driven into the cavity, the boss having surfaces for receiving corresponding tines of a driving tool.

17. In combination, a probe for enabling intracranial pressure in the subarachnoid space to be determined, the probe being inserted through an opening in the scalp, into and through the outer table, diploe and inner table of the skull and dura mater and into the subarachnoid space, the probe comprising:

a threaded shaft having a lumen communicating with opening means at the proximal end of the lumen into the subarachnoid space so that the subarachnoid fluid is coupled into and through the shaft opening means into the lumen and can be coupled thence to a pressure transducer, the threaded portion of the shaft having a length sufficient to threadingly engage the outer table, the diploe and the inner table, the distal end of the shaft including a boss having a central opening aligned with and in fluid flow relation with the lumen; and a tool for driving the probe into place, the tool including a longitudinal axis on which a central stub is located for interlocking with the central opening on the boss, the tool including radially displaced tines extending in the direction of the tool longitudinal axis for engaging outer surfaces of the boss so that the probe is turned and screwed into the skull when the tool is turned about the longitudinal axis thereof while the stub engages the central opening and the tines engage the boss outer surfaces and the probe is in the scalp opening.

* * * * *